(12) United States Patent
Duncan (10) Patent No.: US 8,517,989 B2
(45) Date of Patent: Aug. 27, 2013

(54) MEDICATION INFUSION KIT

(75) Inventor: David R. Duncan, Penryn, CA (US)

(73) Assignee: Monumedical LLC, Citrus Heights, CA (US)

( * ) Notice: Subject to any disclaimer, the term of this patent is extended or adjusted under 35 U.S.C. 154(b) by 16 days.

(21) Appl. No.: 13/160,279

(22) Filed: Jun. 14, 2011

(65) Prior Publication Data
US 2011/0306928 A1 Dec. 15, 2011

Related U.S. Application Data

(60) Provisional application No. 61/397,642, filed on Jun. 14, 2010.

(51) Int. Cl.
*A61M 37/00* (2006.01)

(52) U.S. Cl.
USPC .......................................................... 604/143

(58) Field of Classification Search
USPC ................. 604/140, 141, 143, 146, 147, 149; 206/557, 561, 564
See application file for complete search history.

(56) References Cited

U.S. PATENT DOCUMENTS

| | | | |
|---|---|---|---|
| 3,329,261 A * | 7/1967 | Serany, Jr. et al. | 206/229 |
| 4,128,173 A * | 12/1978 | Lazarus et al. | 206/570 |
| 4,180,067 A | 12/1979 | Derlien | |
| 4,595,102 A * | 6/1986 | Cianci et al. | 206/572 |
| 4,658,957 A | 4/1987 | Guth et al. | |
| 4,966,585 A | 10/1990 | Gangemi | |
| 5,024,664 A | 6/1991 | Mitchell | |
| 5,059,182 A | 10/1991 | Laing | |
| 5,135,500 A | 8/1992 | Zdeb | |
| 5,290,259 A | 3/1994 | Fischer | |
| 5,505,709 A | 4/1996 | Funderburk et al. | |
| 5,807,337 A | 9/1998 | Yamada et al. | |
| 5,810,202 A | 9/1998 | Hoback | |
| 6,012,586 A * | 1/2000 | Misra | 206/571 |
| 6,056,724 A | 5/2000 | Lacroix | |
| 6,139,530 A | 10/2000 | Hiejima | |
| 6,283,943 B1 | 9/2001 | Dy | |
| 6,685,673 B2 | 2/2004 | Minezaki | |
| 7,041,081 B2 | 5/2006 | Minezaki | |
| 7,976,505 B2 | 7/2011 | Hines et al. | |
| 7,993,326 B2 | 8/2011 | Massengale et al. | |
| 2005/0098470 A1 | 5/2005 | Davis et al. | |
| 2006/0283745 A1 | 12/2006 | Massengale et al. | |
| 2009/0198217 A1 * | 8/2009 | Thorne et al. | 604/518 |
| 2010/0305507 A1 | 12/2010 | Duncan | |

* cited by examiner

*Primary Examiner* — Aarti B Berdichevsky
(74) *Attorney, Agent, or Firm* — Law Offices of David M. Lang; David M. Lang (57) ABSTRACT

Embodiments of the present invention include a self-powered infuser with a medicament containing vessel coupled to the infuser capable of exerting sufficient pressure to cause a medicament to flow from the containing vessel, through intravenous tubing, and into a patient's circulatory system. The infuser and vessel may be contained within a sealable kit which may have a separate container for perishable medications such that the medications may be inspected and changed without exposing the remainder of the kit's contents. The infuser may be recyclable or disposable.

3 Claims, 9 Drawing Sheets

MEDICATION INFUSION KIT

CROSS-REFERENCE TO RELATED APPLICATIONS

This application claims the benefit under 35 U.S.C. §119 (e), to U.S. Provisional Application U.S. 61/397,642 filed Jun. 14, 2010, entitled "DISPOSABLE MEDICATION INFUSION KIT" which is incorporated by reference in its entirety and made part of this specification.

FIELD OF THE INVENTION

The present invention relates generally to the field of medicine and therapeutic medication delivery, and more particularly to self-contained parenteral infusion kits.

BACKGROUND

The current practice of intravenous medication infusion often involves a relatively complicated process of assembling several sterile parts and performing appropriate dosing calculations. Further, where more refined dosing is required or desired, expensive electronic infusion pumps are often utilized. Infusion pumps offer certain advantages, but drawbacks include cost, the need for a power source, maintenance requirements, susceptibility to adverse environmental conditions, and perhaps most importantly, require requisite knowledge to use safely and effectively. There are several circumstances where less expensive yet automated intravenous infusion systems are ideal.

Intravenous infusions are now more commonly performed in prehospital settings where smaller, lighter, and self-powered systems enjoy a distinct advantage. In the prehospital setting, equipment storage space is minimal, power may be nonexistent, and equipment must be portable and able to withstand the elements. Yet, emerging data suggests that early prehospital use of certain medications may improve outcome. For example, the early administration of Progestins may improve patient clinical outcome following traumatic brain injury and stroke. Progestins, however, must be infused over a significant duration and should be started early. This ideal window exists at a time when a single paramedic is responsible for performing multiple tasks to stabilize the patient, limiting the time available to manage an intravenous medication system.

Furthermore, administering intravenous medication in other prehospital settings, such as military environments, produces still greater challenges. In addition to the difficulties encountered above, personnel may be scarce, and patients can suddenly and frequently outnumber trained clinical staff. In some locations, the highest level of immediate care is quite commonly a field medic. Further, calamitous events such as natural disasters, war, and insurrection may displace a vast number of people and commonly degrade, destroy, and overwhelm the local hospital system, making medication infusion using standard pumps impossible.

Yet, developing a viable portable intravenous system poses challenges. Infusion pumps are typically too complicated and expensive to dedicate for use with a single medication or make disposable. Traditional pre-packaged and sealed medical and surgical kits have limitations. For example, medications are commonly required in kits, and when a medication's shelf life expires, a typical kit is no longer useful for patient care and frequently must be destroyed. This practice is expensive, wasteful, and presents logistical burden of accounting for and managing medical waste.

Therefore, what is needed is a relatively small, portable, self-contained, and self-powered system which can reliably deliver an intravenous infusion safely and effectively. What is further needed is a kit which contains medications permitting more rapid setup and delivery of an intravenous system, while allowing medications to be inspected and replaced without exposing the remainder of the kit.

SUMMARY

Aspects of the present invention disclose a sterile or non-sterile sealed infusion kit which may be recyclable or disposable, and which may be operated without an AC electric power source. Embodiments of the present invention include a prepackaged infusion kit which may be utilized with or without prepackaged medicaments. Other embodiments describe prepackaged medications contained with the infusion system. Further still, other aspects of the invention disclose a prepackaged system containing specific medication dosages allowing for a more rapid, efficient, and safe infusion. Other aspects of the invention disclose a variety of self-powered force applicators to drive medication from the inventive infuser into the patient's system. Other aspects of the invention describe a kit containing perishable medications or adjunctive solutions wherein a portion of the kit may be opened to expose the perishable substances so they may be changed without opening the remainder of the kit.

DETAILED DESCRIPTION

Figure 1:
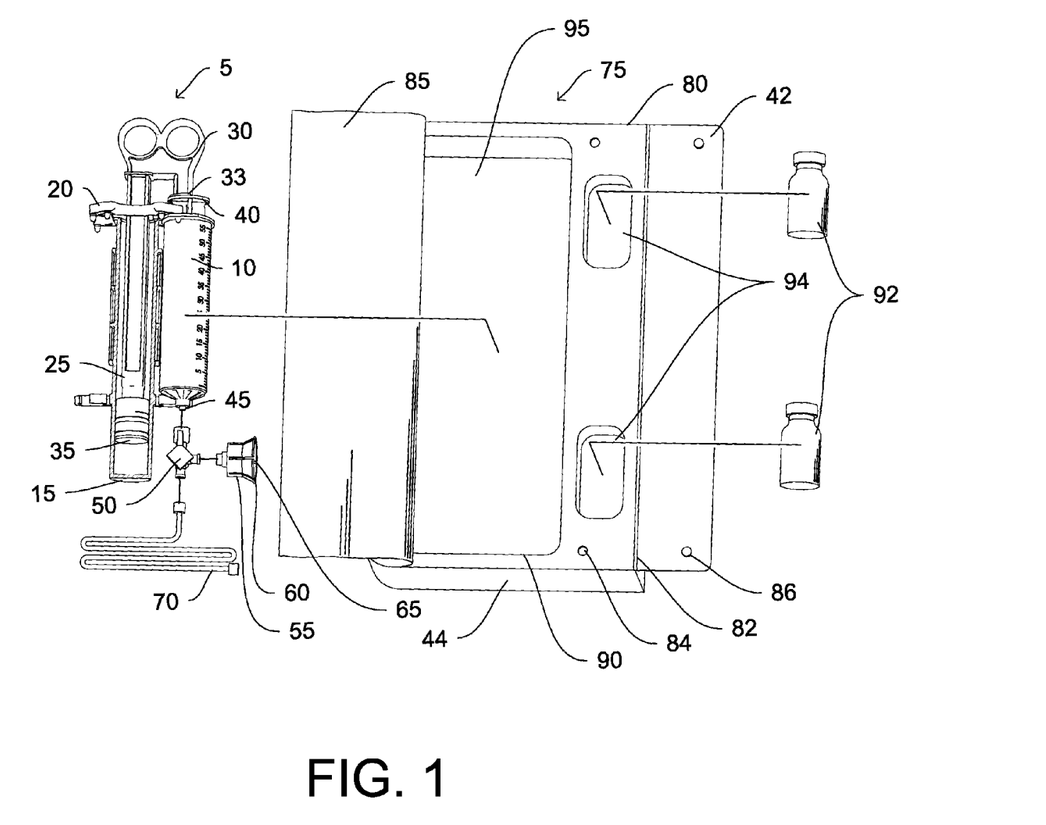
FIG. 1 is a partially exploded perspective view of an embodiment vacuum drive infuser with an embodiment packaging.

Turning now to FIG. 1, infuser 5 may be comprised of a medication holding vessel, such as a syringe 10 coupled to chamber 15 by clamp 20. Driver 25 is attached to or integrally formed with a portion of handle 30 disposed within chamber 15 and an airtight seal is formed between sliding sealed piston 35, mounted on the end of driver 25, and the inner surface of chamber 15. When handle 30 is drawn back, piston 35 increases a vacuum force within that portion of chamber 15 distal to piston 35. In an alternative embodiment, handle 30 is shaped to define a platform 33 which makes contact with the most proximal surface of plunger 40. In an alternative embodiment, a portion of handle 30 is shaped to form plunger 40 which is in a fluid tight disposition within syringe 10. Clamp 20 holds syringe 10 and chamber 15 tightly together in place to prevent movement of syringe 10 relative to chamber 15.

Functionally, the user places medication vial 92 into standard vial adapter 55, during which sharp center spike 65 penetrates the membrane of vial 92. A standard medical stopcock 50 is then oriented to allow the medicament in vial 92 to flow into syringe 10 during standard aspiration of plunger 40, after first rotating handle 30 so that platform 33 and plunger 40 are no longer in contact. After the desired amount of medicament has been aspirated into syringe 10, stopcock 50 is then adjusted to eventually permit the flow of medicament in syringe 10 out of syringe opening 45 and preferably into infusion tubing 70. It should be noted that stopcock 50 may be a two-way, three-way, four-way, or six-way stopcock.

The practitioner then withdraws infuser handle 30 wherein piston 35 is drawn back to produce or increase a vacuum in chamber 15. Next, handle 30 may be rotated to allow driving platform 33 to make contact with and push downwardly on syringe plunger 40. Handle 30 is then released and the force generated by piston 35 sliding forwardly to fill the vacuum causes driver 25 and handle 30 to likewise move forwardly and in so doing, drives platform 33 to depress plunger 40. As plunger 40 moves forwardly within syringe 10, a flowable medicament may flow from syringe opening 45 and out of syringe 10 into any attached intravenous tubing 70 or other route of intravenous administration.

In a preferred embodiment, stopcock 50 and vial adapter 55 may be assistive in controlling flow in and out of syringe 10 by permitting syringe 10 to be filled with medication. For example, stopcock 50, having a first port, second port, and a third port, or more, may be coupled to syringe via luer lock (or other coupling) and opened to provide flow between syringe 10 and vial adapter 55. Vial adapter 55 has an outer housing 60 and inner spike 65 capable of piercing the membrane on a standard medication vial. A vial may be inserted along adapter 55 wherein spike 65 pierces the membrane surface of the vial. The user may then actuate stopcock 50 to permit flow from syringe 10 through tubing 70 which is connected by luer lock or other connector. As syringe 10's plunger 40 moves forwardly medication is forced from syringe 10 through stopcock 50 and through tubing 70 and thereafter into a patient's circulatory system.

In a preferred embodiment, infuser 5, or any embodiment infuser described hereinafter, may be disposed within a sealable packaging 75. Packaging 75 is comprised of a tray 80 which is shaped to define at least one indentation, recess or well to accommodate kit items, and removable covering 85 that seals tray 80's top surface 90. Infuser 5 may be disposed within first well 95. One or more vials 92 may be disposed in one or more medicament wells 94 which may be identically or differently shaped and correspond to the size and shape of the appropriate vials 92 or other medicament containers to be stored within. Stopcock 50, vial adapter 55 and tubing 70 may be stored in the first well 95 or in an alternative embodiment, wells shaped to provide adequate individual storage. In one embodiment, medicaments such as vials 92 are independently sealed by foldable flap cover 42 which folds along seam 82 and may be locked into place by a fittable engagement of projections 86 and recesses 84. Medication cover 42 may be opened and closed independently of cover 85, wherein cover 85 may remain sealed as medication cover 42 is opened and closed. Medication cover 42 may be transparent or partially transparent to permit ready medication viewing while medication cover 42 is in the closed position with projections 86 fittably engaged within recesses 84. In this way, written packaging materials and indicia appearing on the surface of vial 92 (or other medicaments disposed within medication recess 94) may be inspected. Information such as medication expiration dates, lot number, and the like may be inspected without opening the packaging. Should it become necessary to change the medicament, medication cover 42 may be opened—removing projections 86 from recesses 84 and medication cover 42 is folded outwardly and reflected to expose medication wells 94. After medication has been replaced, cover 42 may be folded inwardly and closed by snap fitting projections 86 within recesses 84.

In an alternative embodiment, the first well 95 is covered with a first cover 85, and one or more medicament wells 94 are covered with a second cover. One or more of the covers covering any wells may be re-sealable. Alternatively, each well may have its own cover which may be re-sealable.

Figure 2:
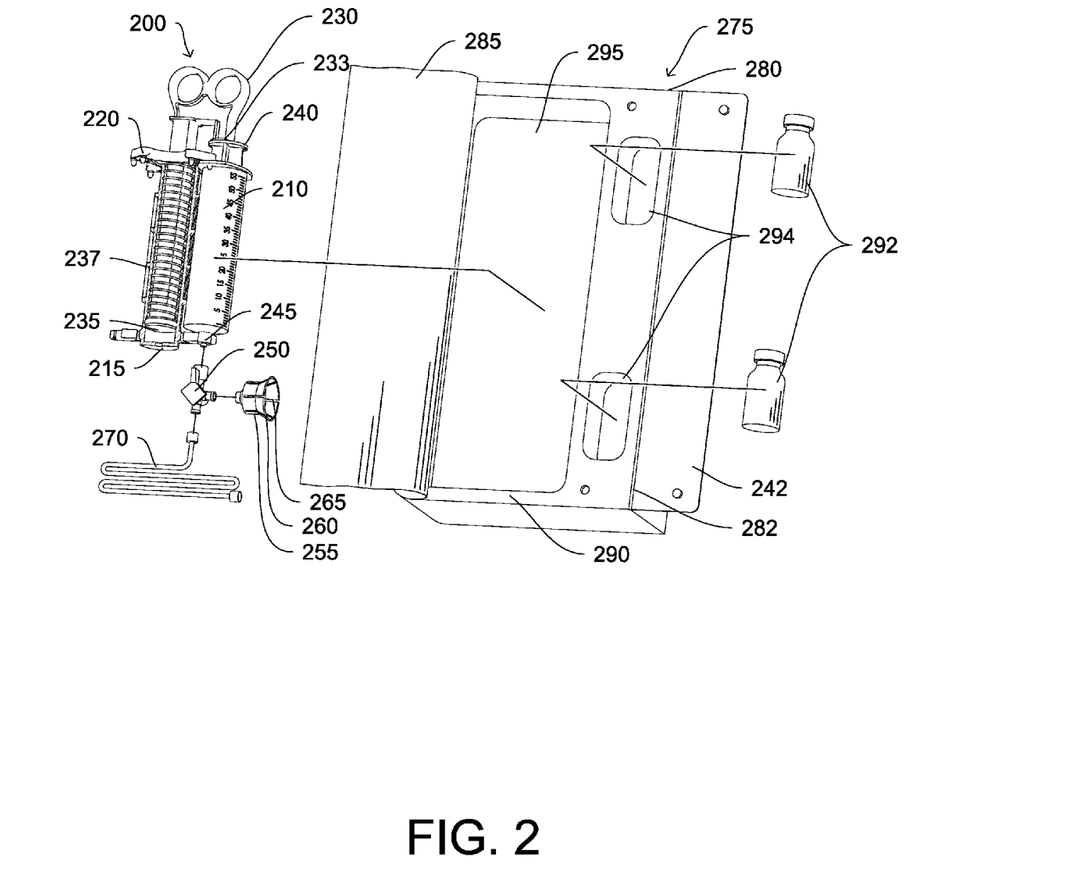
FIG. 2 is a partially exploded perspective view of an embodiment spring-drive infuser with an embodiment packaging.

Turning now to FIG. 2, an alternative embodiment spring-driven infuser 200, may be comprised of a syringe 210 coupled to chamber 215 by clamp 220. Handle 30 is shaped to define a platform 233 which makes contact with the most proximal surface of a plunger 240 found in a typical syringe. In an alternative embodiment, a portion of handle 230 is shaped to form plunger 240. Driver 225 is attached to a portion of handle 230 disposed within chamber 215 and terminates in piston 235. Spring 237 is disposed around driver 225 and has a first end affixed to clamp 220 and second end affixed to the proximal portion of piston 235.

In a preferred embodiment, infuser 200 may be disposed within a sealable packaging 275. Packaging 275 is comprised of a tray 280 which is shaped to define at least one indentation, recess or well to accommodate kit items, such as well 295, and removable covering 285 seals tray 280's top surface 290. Cover 242 may be folded along seam 282 and closed as described above.

Functionally, the user withdraws handle 230 wherein piston 235 is drawn back to produce compression in spring 237. Compression in spring 237 acting on the proximal side of piston 235, biases piston 235, driver 225, and handle 230 forwardly. A portion of handle 230 is shaped to form driver platform 233 which makes contact with and depress plunger 240, which is driven forwardly. In an alternative, a portion of handle 230 is shaped to define an integrally formed plunger. As plunger 240 moves forwardly, a flowable medicament may flow from syringe opening 245 and out of syringe 210.

Figure 3:
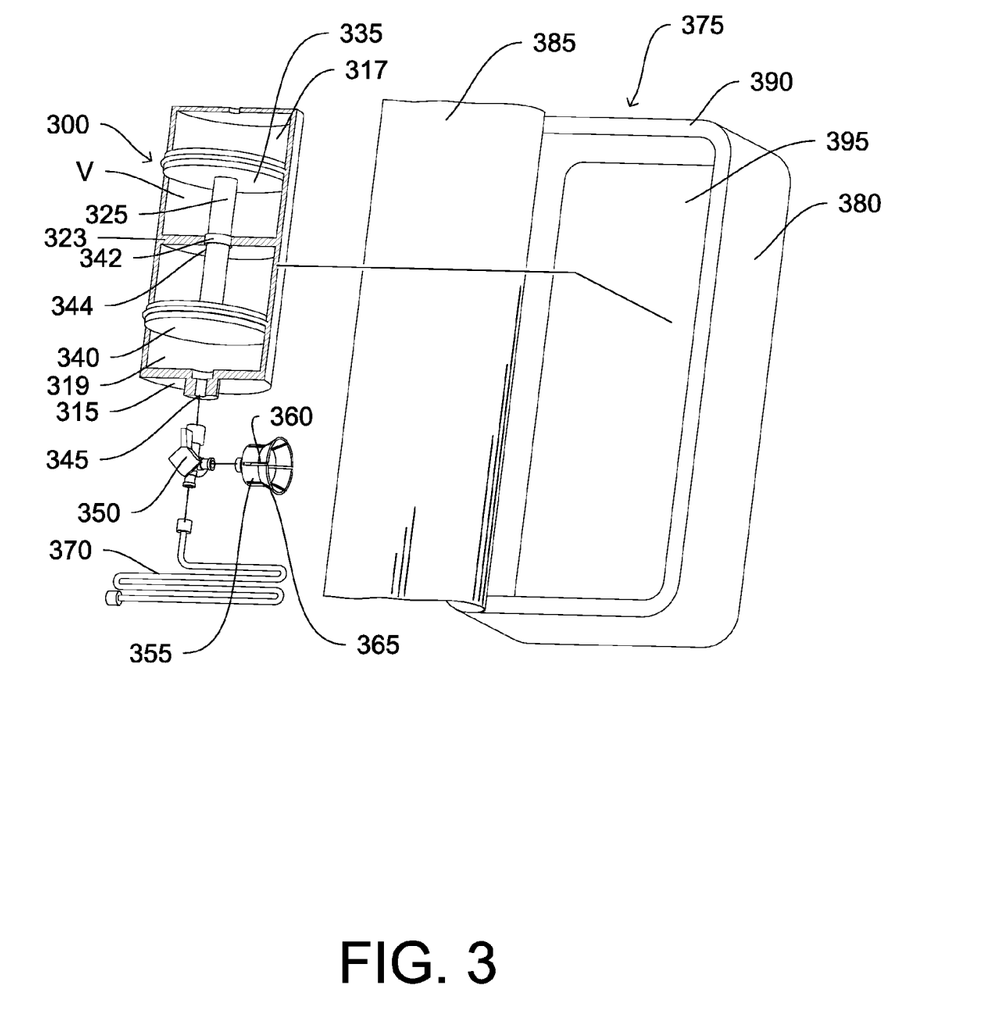
FIG. 3 is a partially exploded perspective view of an embodiment coaxial vacuum powered syringe with an embodiment packaging.

Turning now to FIG. 3, coaxial vacuum powered syringe infuser 300 may be comprised of chamber 315 segmented into driver housing 317 and plunger housing 319 by a portion of chamber 315 shaped to define divider 323. Shaft 325 is coupled to piston 335 disposed within driver housing 317 and plunger 340 within plunger housing 319. Shaft 325 is disposed and moves within airtight shaft seal 342; shaft seal 342 itself being disposed within aperture 344 of divider 323. The circumferential surface of piston 335 and plunger 340 may be rubberized to provide an airtight seal in driver housing 317 and at least a fluidtight seal in plunger housing 319. Chamber 315 is formed with vacuum V existing between the surface of piston 335 and the surface of divider 323 tending to drive piston 335 and divider 323 into contact. It should be noted that in a preferred embodiment, piston 335, shaft 325, and plunger 340 are integrally formed as a single coaxial driver.

Functionally, the user may fill plunger housing 319 with a flowable medicament. This is accomplished a variety of ways, for example, by attaching a standard syringe to opening 345 and forcing medication out of the standard syringe into plunger housing 319 or by attaching a syringe to stopcock 350 and actuating it to provide flow between stopcock 350 and plunger housing 319. The force of vacuum V is overcome by the force driving medication into plunger housing 319, and plunger 340, shaft 325, and piston 335 together move backwardly plunger housing 315 is filled distally to plunger 340. When vacuum force V is greater than the opposing resistance, medicament may flow from housing 319 through opening 345 and stopcock 350 and tubing 370 when attached.

In a preferred embodiment, infuser 300 may be disposed within a sealable packaging 375. Packaging 375 is comprised of a tray 380 which is shaped to define at least one indentation, recess, or well to accommodate kit items, such as well 395, and removable covering 385 seals tray 380's top surface 390. Infuser 300 and optionally stopcock 350, vial adapter 355 and tubing 370 may be stored in first well 395 or in an alternative embodiment, wells shaped to provide adequate individual storage.

Figure 4:
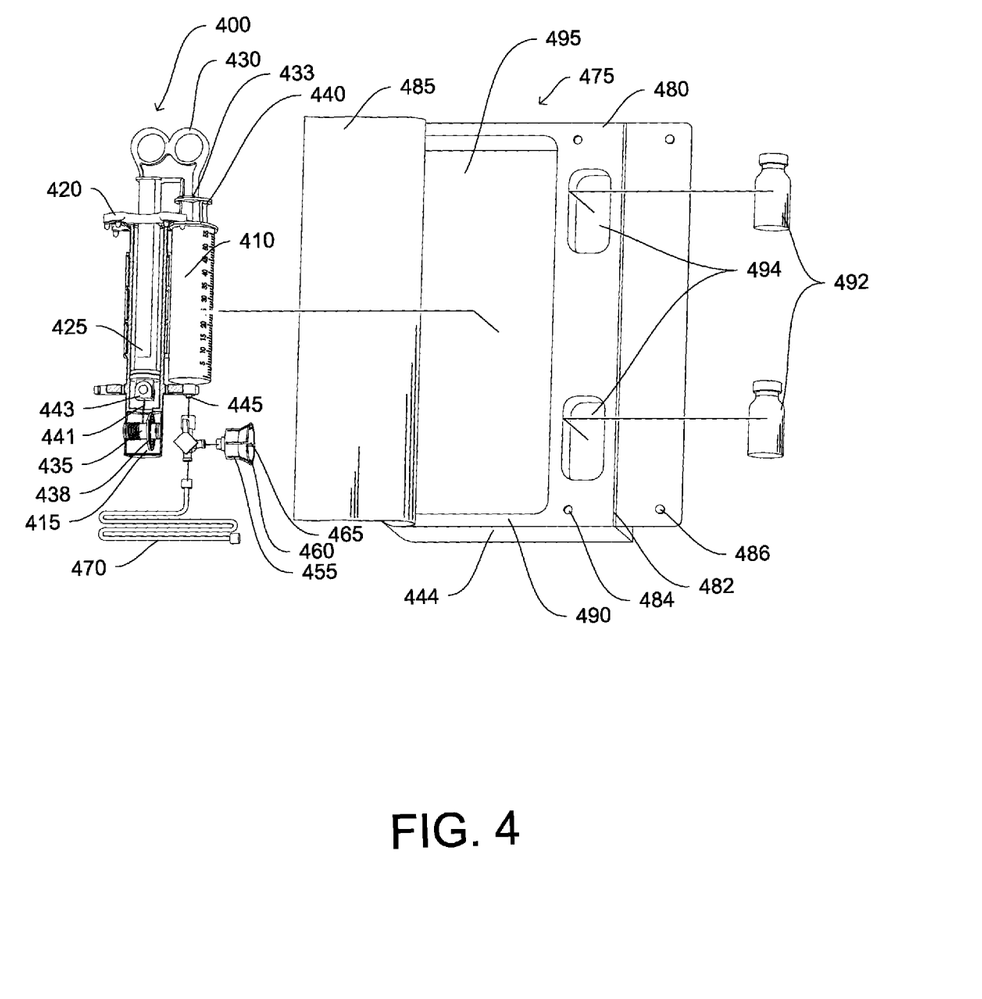
FIG. 4 is a partially exploded perspective view of an embodiment spring-driven infuser, with embodiment packaging.

Now, FIG. 4 demonstrates infuser 400 which may be comprised of a syringe 410 coupled to chamber 415 by clamp 420. Driver 425 is attached to or integrally formed with a portion of handle 430 disposed within chamber 415. Spring axle 435 is disposed within a relatively distal aspect of chamber 415 and freely rotatable therein. Flat torsion coil power spring 438 is affixed to axle 435 under tension to bias rotation. Wire 441 is affixed to axle 435 at one end and coupling 443 at the other end. Coupling 443 is affixed to the terminal aspect of driver 425. When coil spring 438 rotates axle 435, wire 441 is wound onto axle 435 and wire 441 applies a traction force to drive driver 425, handle 430, and handle platform 433 forwardly within chamber 415.

Functionally, the user withdraws handle 430 wherein piston 435 is drawn back to increase tension in spring 438, as driver 425 and wire 441 affect rotation of axle 435. Syringe 410 may be filled with a flowable medicament by the standard means of aspiration. When the desired volume of medicament has been collected within syringe 410, handle 430 is energized by pulling handle 430 back, following which, handle 430 is rotated sufficiently to engage driver platform 433 and plunger 440. When handle 430 is released, the force generated by driver 425 moving forwardly drives handle 430, platform 433, and depresses plunger 440 forwardly causing medication to flow from within syringe 410 through opening 445.

Figure 5:
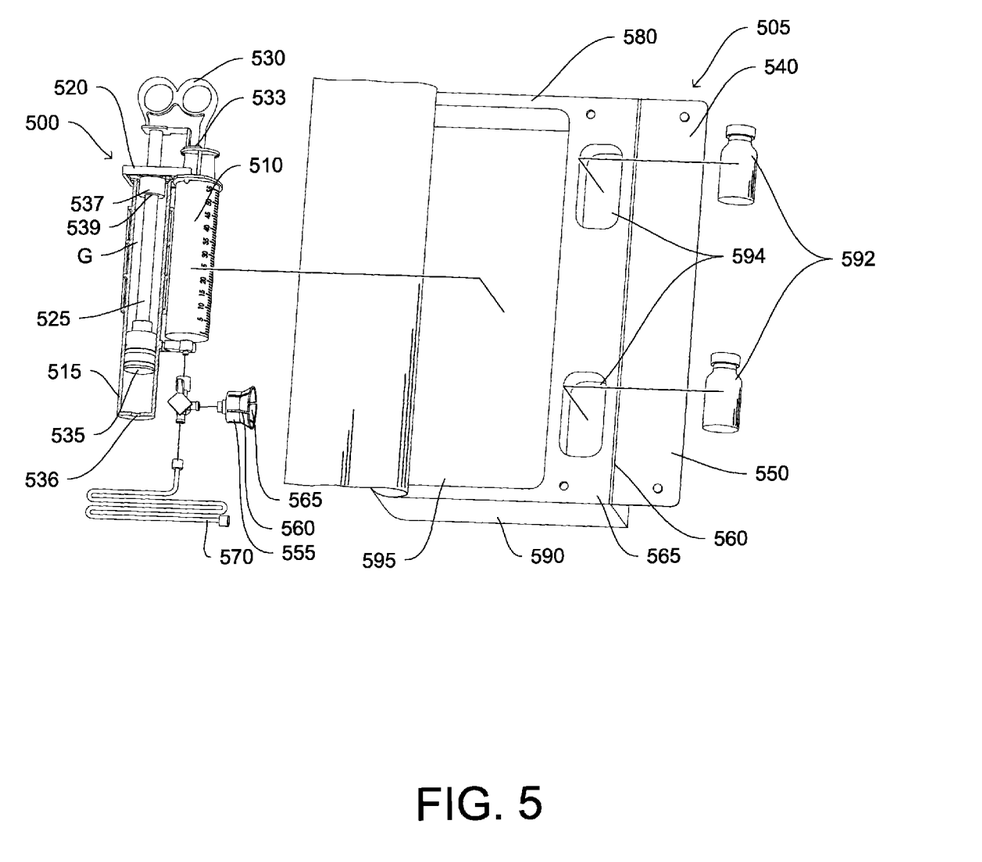
FIG. 5 is a partially exploded perspective view of an embodiment gas-driven infuser, with embodiment packaging.

Turning now to FIG. 5, infuser 500 may be comprised of a syringe 510 coupled to chamber 515, the chamber having a top and bottom, by clamp 520. Driver 525 is attached to a portion of handle 530 and disposed within chamber 515. Sliding sealed piston 535 is mounted on the end of driver 525, and a seal is formed between sliding sealed piston 535 and the inner surface of chamber 515 and cap 537 seals the top of chamber 515. Driver 525 passes through aperture 539 in cap 537 with driver 525 and cap forming an airtight seal. Gas, such as CO2, nitrogen, or air, pressurizes the chamber 515 such that gas pressure G exerts positive pressure between cap 537 and piston 535 to drive driver 525 forwardly. The terminal aspect of chamber 515 has opening 536 to provide air to move in and expelled from chamber 515 distal to piston 535. A portion of handle 530 is shaped to define platform 533 which makes contact with the most proximal surface of a plunger 540 found in a typical syringe. In the alternative, a portion handle 530 is shaped to define an integrally formed plunger disposed forming a syringe.

Functionally, the user withdraws handle 530 wherein piston 535 is drawn back to further compress the gas G in chamber 515, raising the pressure and energizing the apparatus. The syringe 510 may be filled with a flowable medicament in the usual way from medicament vial 592, by aspirating the medicament through stopcock 550 into the syringe when the medicament vial 592 is spiked onto vial adapter 555. When syringe 510 has been filled with the desired amount of medication, handle 530 is rotated to place platform 533 into alignment with plunger 540 and released. The force generated by piston 535 sliding forwardly, driven by the force of compressed gas G, causes driver 525 and handle 530 to likewise move forwardly and in so doing, drive plunger 540 within syringe 510. As plunger 540 moves forwardly, a flowable medicament may flow from syringe opening 545 and out of syringe 510.

Figure 6:
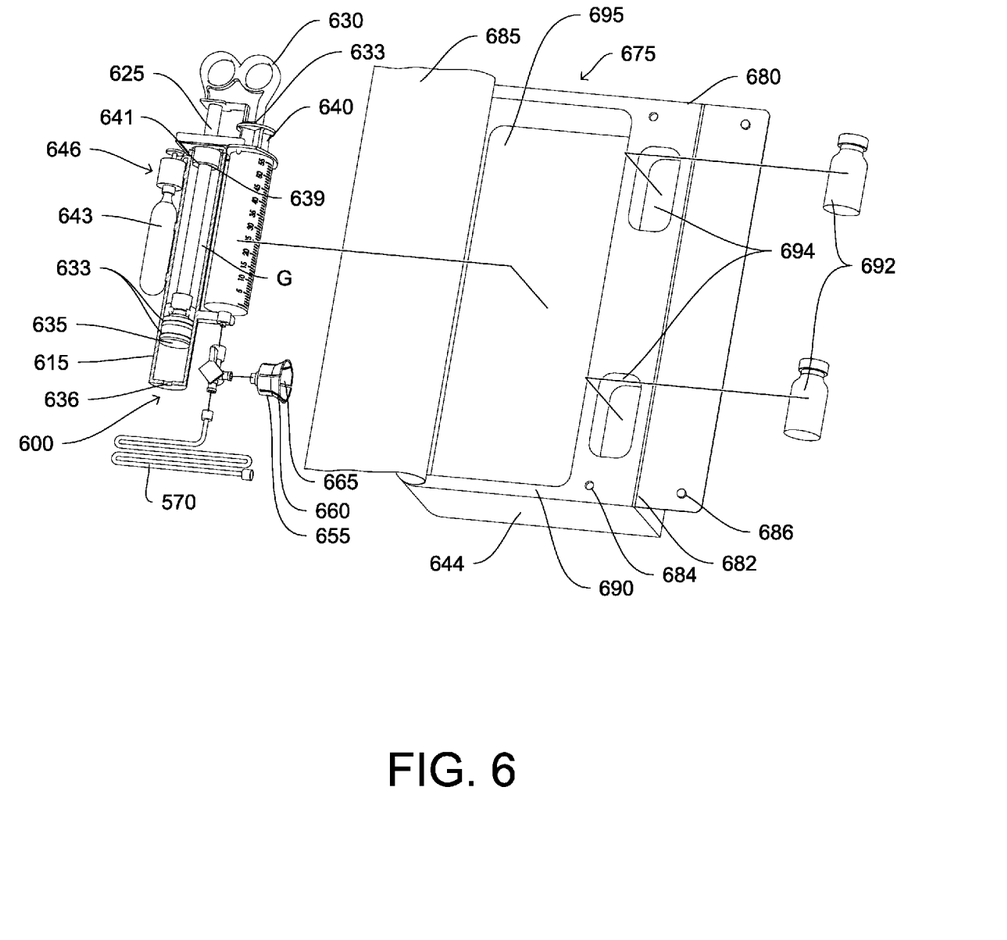
FIG. 6 is a partially exploded perspective view of an embodiment gas-driven infuser, with embodiment packaging.

FIG. 6 illustrates infuser 600 which may be comprised of a driver 625 coupled to piston 635 disposed with chamber 615. A seal, such as one or more O-rings 633 are located on the circumferential surface of piston 635 to provide a seal. Driver 625 is attached to a portion of handle 630 shaped to define platform 633 that makes contact with a standard syringe. Driver 625 passes through aperture 639 sealed with O-ring 641 such seal being airtight. Gas, such as CO2, nitrogen, or air, is stored within cylinder 643 flows through regulator 646 into pressurize chamber 615; gas pressure G exerts positive pressure to drive driver 625 forwardly. A portion of handle 630 is shaped to define a platform 633 which makes contact with the most proximal surface of a plunger 640 of a typical syringe.

Functionally, gas G flows from cylinder 643 through regulator 646 into chamber 615, raising pressure. When the force of gas pressure G exceeds the force of the piston's static resistance (i.e. between of piston 635 and chamber 615) and the forces acting on platform 633, piston 635 will move forwardly to drive platform 633 and any standard syringe plunger 640 in contact therewith. Regulator 646 maintains a constant pressure in chamber 615 so that the pressure force remains the same throughout the infusion cycle.

Figure 7:
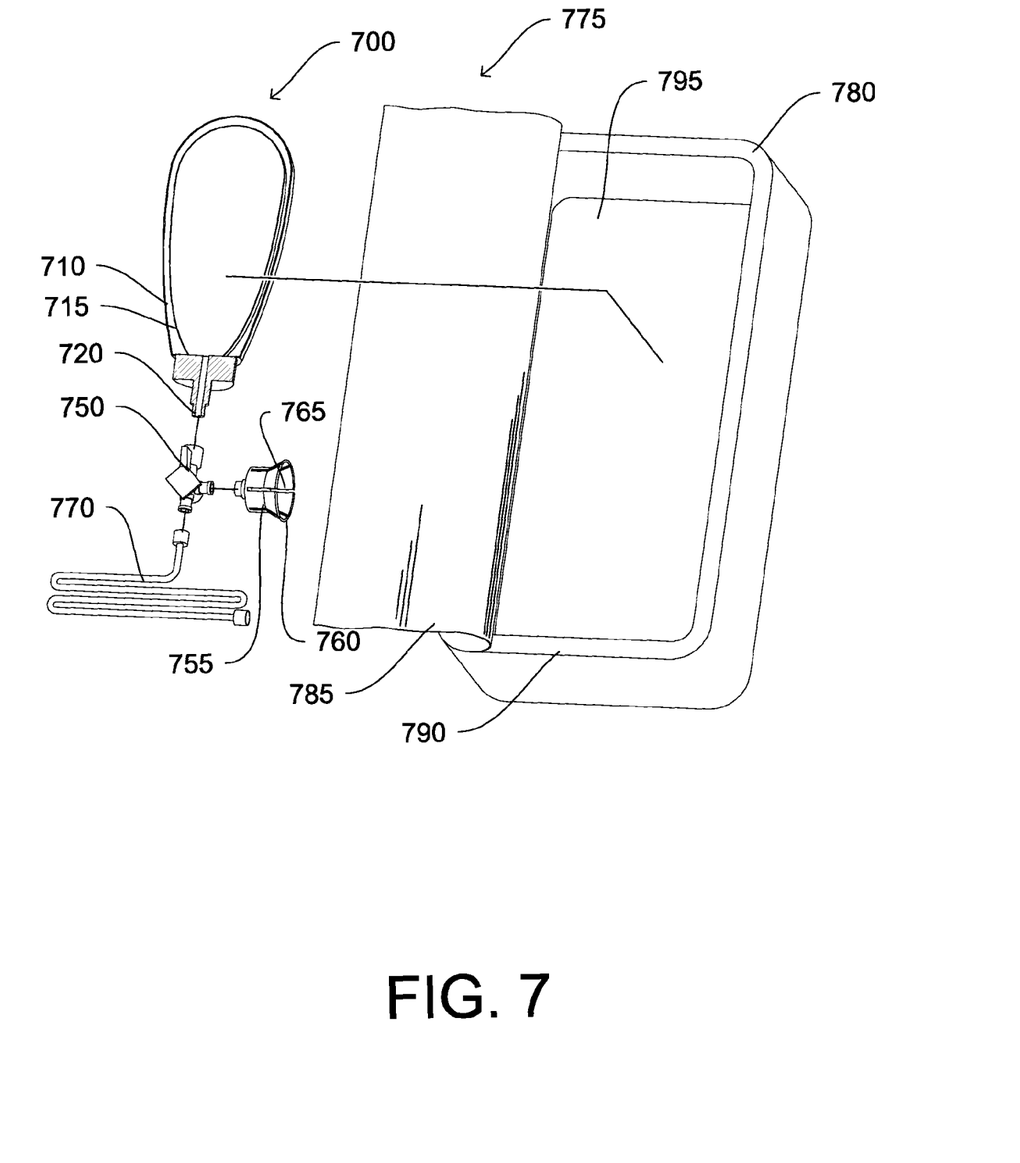
FIG. 7 is a partially exploded perspective view of an embodiment elastomeric balloon, with embodiment packaging.

Turning now to FIG. 7, infuser 700 consists of a single or double walled elastomeric balloon 710 having an internal reservoir 715 capable of holding medication. Balloon 710 terminates in a coupling 720 capable of reversibly attaching to stopcock 750, intravenous tubing 770, or a standard syringe. Filled elastomeric balloon 710 has sufficient resiliency to generate an effective amount of force to drive a medicament through tubing 770. A medicament may be prepackaged within reservoir 715 or reservoir 715 may be filled by a standard syringe.

In a preferred embodiment, infuser 700 may be disposed within a sealable packaging 775. Packaging 775 is comprised of a tray 780 which is shaped to define at least one indentation, recess or well to accommodate kit items, such as well 795, and a removable covering 785 seals tray 780's top surface 790. Infuser 700 and optionally stopcock 750, vial adapter 755 and tubing 770 may be stored in first well 795 or in an alternative embodiment, disposed within wells shaped to provide adequate individual storage.

Figure 8:
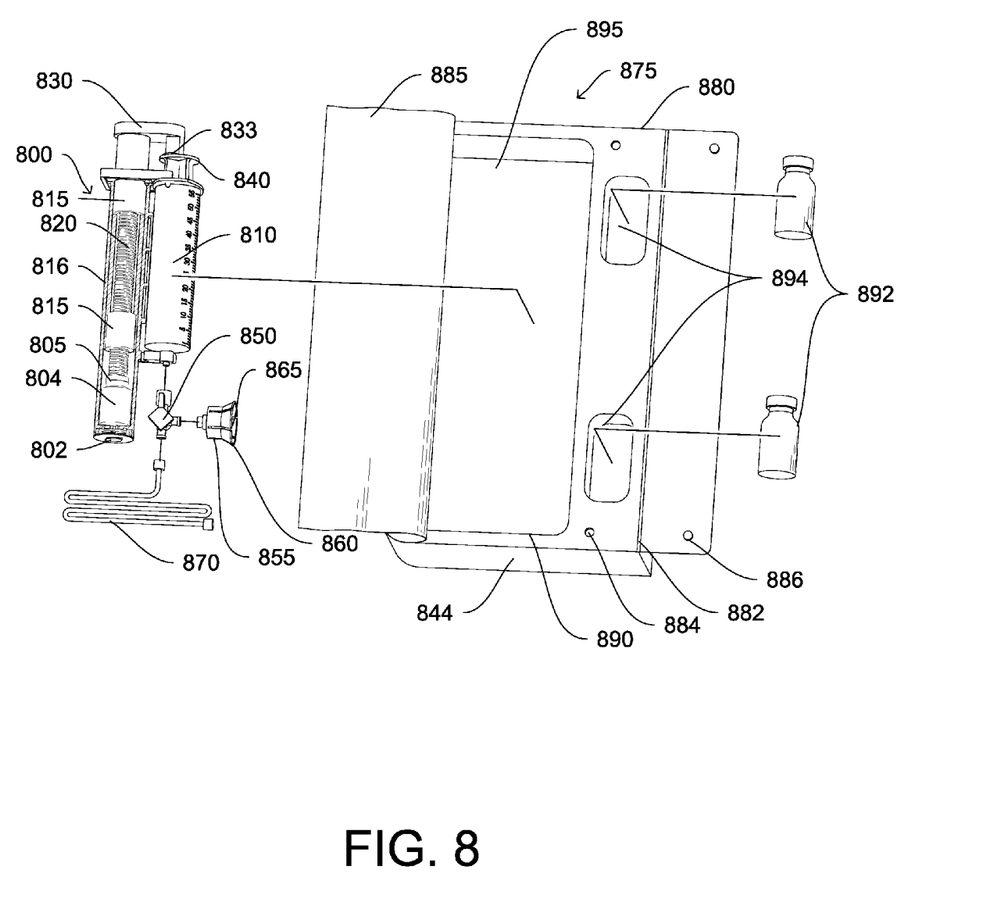
FIG. 8 is a partially exploded perspective view of an embodiment motor driven infuser with a portion of threaded tube removed to expose worm screw, with embodiment packaging.

FIG. 8 illustrates an embodiment infuser 800 having an integrated circuit and attached battery 802 electrically coupled to reversible servo gearhead motor 804. Worm screw 820 is coupled to motor 804 by coupling 805 at screw's first end. FIG. 8 illustrates threaded tube 815 which forms part of driver housing arm 830 and threaded tube 815 is disposed within housing 816. Worm screw 820 is disposed within threaded tube 815. FIG. 8 illustrates a portion of threaded tube 815, with a portion of tube 815 omitted (for illustrative purposes) to show worm screw 820 disposed therein. The second end of screw 820 is disposed within driver arm 830. Platform 833 may make contact with plunger 840 of syringe 810.

Functionally, when circuit is closed, motor 804 actuates to rotatably drive worm screw 820. Worm screw 820 threadably engages threaded tube 815 resulting in worm screw 820 being driven axially forwardly driving arm 830 and platform 833 downwardly to depress plunger 840 and force a flowable medicament from syringe 810. Motor 804 may be reversed to drive worm screw axially backwardly.

In a preferred embodiment, infuser 800 may be disposed within a sealable packaging 875. Packaging 875 is comprised of a tray 880 which is shaped to define at least one indentation, recess or well to accommodate kit items, such as well 895, and a removable covering 885 seals tray 880's top surface 790. Infuser 800 and optionally stopcock 850, vial adapter 855 and tubing 870 may be stored in first well 895 or in an alternative embodiment, disposed within wells shaped to provide adequate individual storage.

Figure 9:
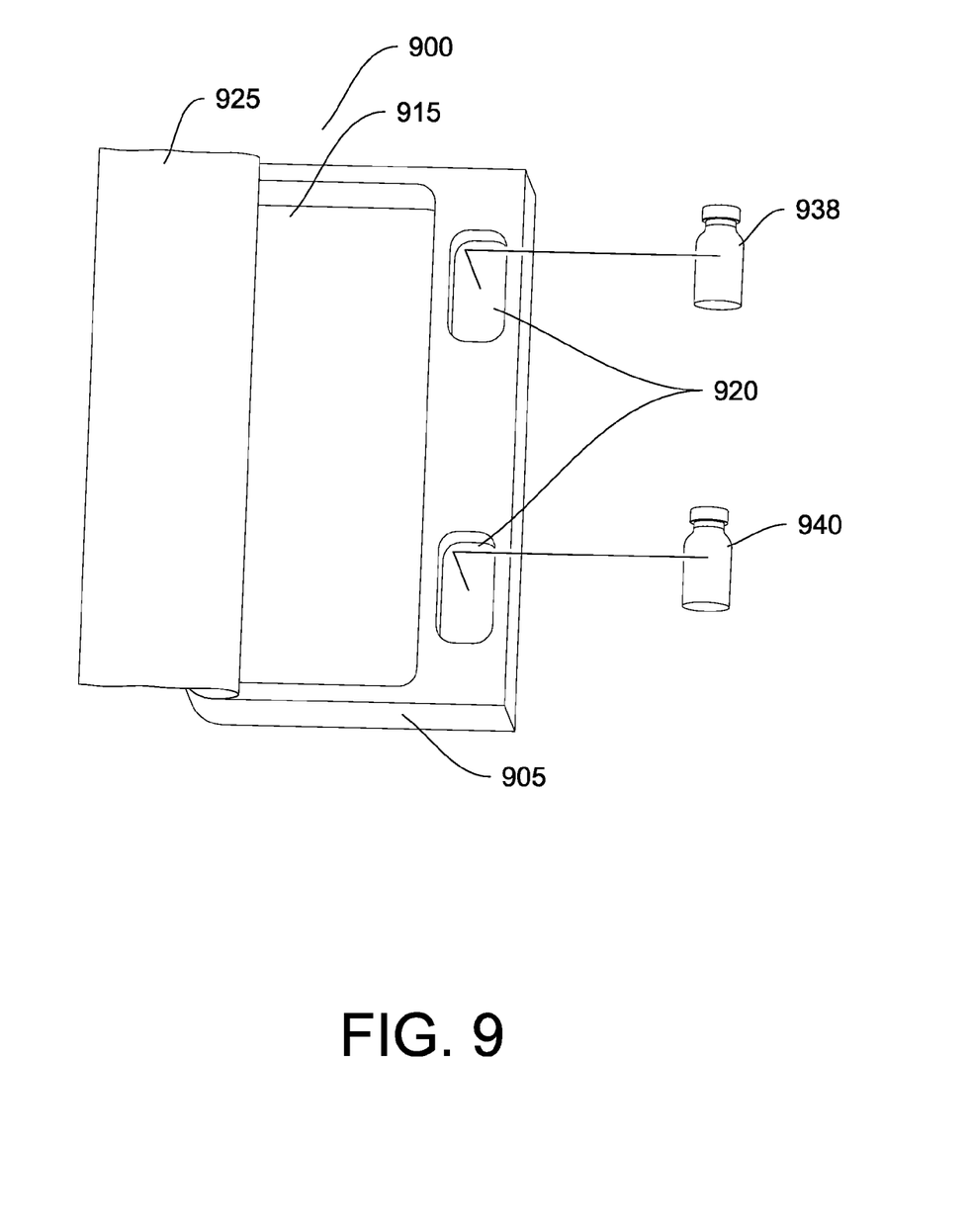
FIG. 9 is a perspective view of an embodiment packaging.

With regard to the kit covering, in an alternative embodiment, illustrated by FIG. 9, seam 82, recesses 84, and projections 84 are omitted, and the top surface is uniform. In one embodiment, the top surface may be covered with a removable covering 925. In one embodiment, covering 925 is a single use cover; in an alternative embodiment, cover 925 is a single reusable cover which may be replaced over the top surface to re-seal all contents within tray 950. It should be realized that tray packaging 900 may be used with medical apparatus and medicaments of all types.

Several example embodiments are described above. The general inventive concepts include use of a force applicator acting on a flowable therapeutic substance or medicament within a vessel. In several of present embodiments described above, the containing vessel is a syringe coupled to several embodiments of a force applicator in a side-by-side or coaxial arrangement. It should be immediately recognized that the location, arrangement, and relative size of the vessel, force applicator, and/or handle may be changed without departing from the spirit and scope of the invention. Further, in several embodiments, an example component of a force applicator includes a handle which forms or engages a portion of a standard syringe.

As is customary, ultimately, the infusion and patient clinical response is monitored by the professional administering the medicament. In some therapeutic settings, the apparatus may be utilized with limited clinician involvement (e.g. infusion of antibiotics). In other settings, the apparatus is utilized with active bedside clinician involvement (e.g. anesthetics or potent analgesics) where patient response is actively monitored, and the infusion may be interrupted when a desirable clinical effect is achieved. As is also customary, the infusion may be interrupted where an undesirable or adverse clinical effect is encountered. It should be recognized that a force applicator may take a variety of shapes and sizes to impart force on a flowable therapeutic substance without departing from the scope and spirit of the present invention.

The term medicament, as used herein, refers to any flowable substance which may have therapeutic benefit. Further, the apparatus described herein may be utilized without regard to intravenous line placement, and may be utilized to provide an infusion through central and peripheral venous access locations. It should be recognized that the system described herein may be utilized to provide infusion through any therapeutically acceptable location, including but not limited to intraosseous, epidural, intrathecal, or intraperitoneal routes.

It should be further recognized, that the present invention may be utilized to facilitate mixture, admixture, or reconstitution of medication, and the embodiment vial housing can be used to facilitate reconstitution of powered medicaments. For example, a diluent vial may be puncturingly engaged on an embodiment vial adapter and stopcock engaged to permit flow between a syringe and vial and permit dilutent aspiration into the syringe. The stopcock may be aligned to close flow between the syringe and vial, and a second vial containing the medicament to be reconstituted puncturingly engaged on the vial adapter whereupon, stopcock may be aligned to permit flow between the syringe and vial to allow dilutent to be instilled into vial where it can be agitated and mixed according to manufacturer's instructions and accepted clinical practices. Further, the number, size, shape, and contents of medication vials may be variable. For example, several vials containing the same substance may be provided where repeat dosing is foreseeable.

Further, the present invention describes, in part, a kit containing medical apparatus to facilitate the infusion of therapeutic substances and medications or adjunctive solutions contained within that kit where the apparatus and medications are separately contained and where the medications may be inspected and accessed without opening that portion of the kit containing apparatus. It should be immediately recognized that the inventive kit herein described may be utilized with any type of medical apparatus capable of being separately sealed.

The syringe and/or force applicator may or may not be have indicia printed or etched thereupon. Examples of such indicia include such information to facilitate accurate medication administration such as cubic centimeters (cc), milliliters (ml), age, weight, and dosing information.

The present invention may be practiced with several medication classes, including, but not limited to: opiates, opioids, sedatives, benzodiazepines, propofol, vasopressors, anesthetics, vasodialators, anticoagulants, antibiotics, antiarrhythmics, antiepileptics, antirheumatic drugs, steroids, chemotherapeutic agents, and progestins. It should be noted that the term medicament, as used herein, refers to any substance which may have a potential health benefit or therapeutic use.

References are made herein to the spatial orientation of the inventive apparatus. Distal and distally are used to refer to points relatively closer to the subject patient (e.g. furthest from handle 225); whereas proximal and proximally referring to points relatively further from the patient (e.g. closest to handle 225). Forwardly and backwardly are used to describe the movement of certain embodiments and forward and forwardly refer to movement in the direction of opening 230 whereas backward or backwardly refer to movement away from opening 230. The inventive infuser embodiments described herein may be practiced with or without the use of the example packaging, and the apparatus described herein may be packaged according to any acceptable custom. Stopcocks, vials, and tubing are described as optional embodiments and may or may not be included used with the inventive infuser/medicament containing vessel.

Although the present invention has been described with reference to the preferred embodiments, it should be understood that various modifications and variations can be easily made by those skilled in the art without departing from the scope and spirit of the invention. Accordingly, the foregoing disclosure should be interpreted as illustrative only and is not to be interpreted in a limiting sense. It is further intended that any other embodiments of the present invention that result from any changes in application or method of use or operation, method of manufacture, shape, size, or material which are not specified within the detailed written description or illustrations contained herein yet are considered apparent or obvious to one skilled in the art are within the scope of the present invention.

I claim:

1. An infusion kit comprising:

an infuser; a medicament containing vessel having an opening capable of receiving and holding a flowable medicament therein, said vessel operatively coupled to said infuser, wherein said infuser is capable of exerting sufficient pressure within said vessel to cause the medicament to flow from said vessel's opening; a tray having a top surface and shaped to define a first well and at least one medicament well; a removable cover sealed over said first well, wherein said infuser comprises: a chamber, a driver disposed with said chamber, a piston mounted on the end of said driver, wherein an airtight seal is formed between said piston and said chamber, a handle integrally formed with said driver, wherein when handle is drawn back, a vacuum force is created within said chamber distal to said piston; a clamp coupled to said chamber; wherein said medicament containing vessel is comprised of a syringe coupled to said chamber by said clamp, wherein syringe and chamber are held tightly together, wherein said tray is shaped to define a seam and foldable flap cover, wherein said foldable flap cover may be folded along said seam and closed to cover said medicament well, wherein said infuser and medicament containing vessel are disposed within the first well; at least one medicament is disposed within said medicament well, wherein said medicament has packaging indicia on its surface; wherein said foldable flap cover may be opened and closed independently of removable cover, wherein removable cover may remain sealed as said foldable flap cover is opened and closed, wherein said foldable flap cover is at least partially transparent, wherein at least a portion of the packaging indicia on the surface of said medicament disposed within said medicament well is viewable while foldable flap cover is in the closed position.

2. The infusion kit of claim 1, further comprising a stopcock capable of being coupled to said medicament containing vessel; a vial adapter capable of being coupled to said stopcock; intravenous tubing capable of being coupled to said stopcock or said medicament containing vessel.

3. The infusion kit of claim 1, further comprising:

a three-way stopcock having a first port, a second port, and a third port, the first port of said stopcock operatively coupled to said vessel's opening, said stopcock disposed within said first well; a vial adaptor operatively coupled to said second port of said stopcock, said vial adaptor disposed within first well; an infusion tubing operatively coupled to the third port of said stopcock, said infusion tubing disposed within said first well; wherein the stopcock may be rotated to obstruct a single port and permit flowable materials to flow between the remaining two ports.

* * * * *